United States Patent [19]
Harvey

[11] Patent Number: 5,220,402
[45] Date of Patent: Jun. 15, 1993

[54] MULTIPLE-PATH GAS-ABSORPTION CELL

[75] Inventor: Robert J. Harvey, Capistrano Beach, Calif.

[73] Assignee: Harvey C. Nienow, Newport Beach, Calif. ; a part interest

[21] Appl. No.: 835,057

[22] Filed: Feb. 11, 1992

Related U.S. Application Data

[63] Continuation of Ser. No. 369,460, Jun. 21, 1989, abandoned.

[51] Int. Cl.$^5$ .............................................. G01N 1/10
[52] U.S. Cl. ...................................... 356/246; 356/440
[58] Field of Search ................ 356/246, 346, 410, 440

[56] References Cited

U.S. PATENT DOCUMENTS

| | | | |
|---|---|---|---|
| 4,322,621 | 3/1982 | Aagaro .................................. | 356/440 |
| 4,421,408 | 12/1983 | Davis et al. ......................... | 356/246 |
| 4,730,112 | 3/1988 | Wong .................................. | 250/343 |
| 4,749,276 | 6/1988 | Bragg et al. ........................ | 356/246 |

FOREIGN PATENT DOCUMENTS 2307298 8/1973 Fed. Rep. of Germany ...... 356/246

OTHER PUBLICATIONS

Long Optical Paths of Large Aperture, White, J.O.S.A., May 1942, pp. 285-288.

Primary Examiner—Samuel A. Turner
Attorney, Agent, or Firm—Harvey C. Nienow

[57] ABSTRACT

A gas-absorption cell for use with spectrophotometric equipment having a generally circular housing or body formed with inlet and outlet openings for the passage therethrough of predetermined types of energy, there being an optical lens in the inlet opening for directing incoming energy to a highly reflective annular surface within the body whereby energy is permitted to reflect back and forth across the interior of the body, thereby making a plurality of different paths through a gas sample before it is caused to leave the cell through the output opening therein. Such cell configuration can be substantially coplanar or it can be in the form of a sphere; in either case, the plurality of paths through the gas includes substantially all of the interior of the cell. Also, two or more substantially coplanar cells can be arranged in juxtaposition with the energy being transferred from one cell to another by suitably positioned reflectors.

9 Claims, 3 Drawing Sheets

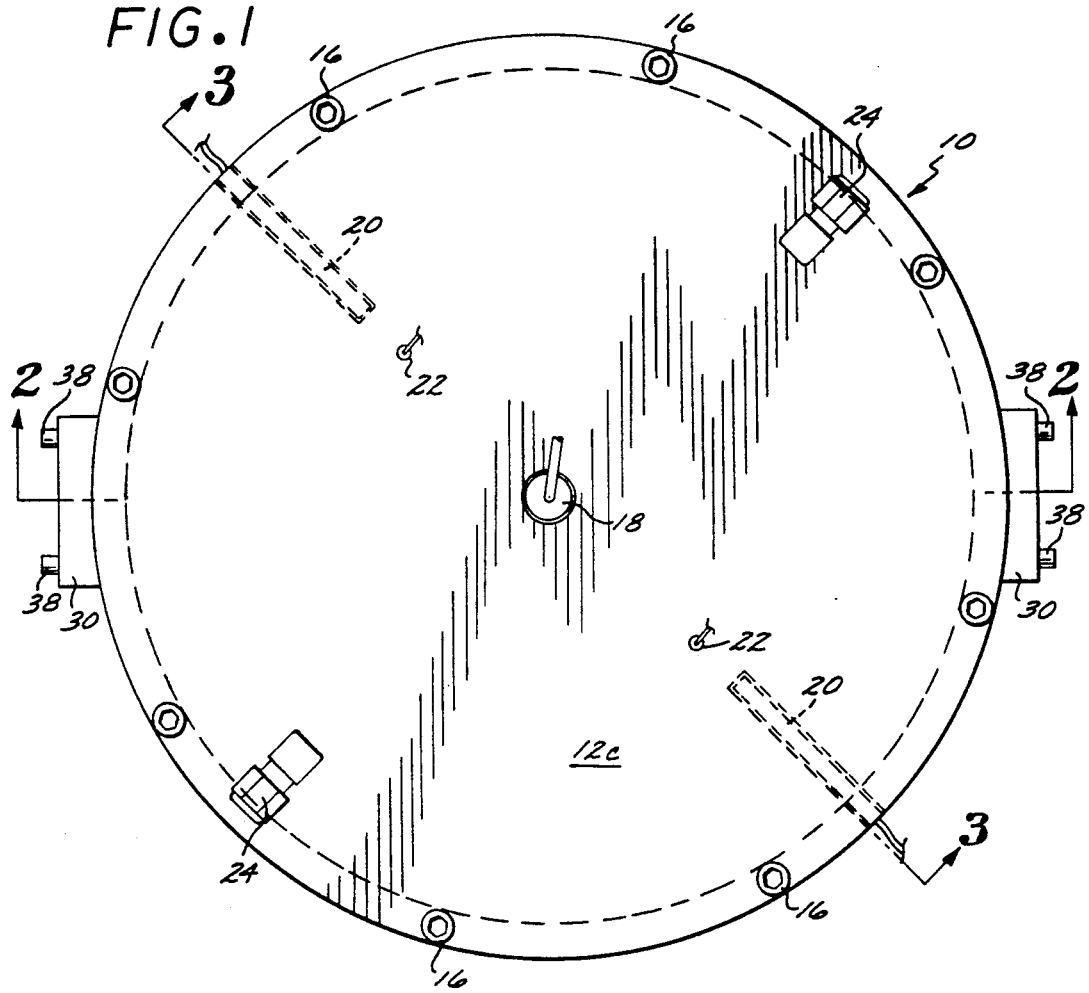
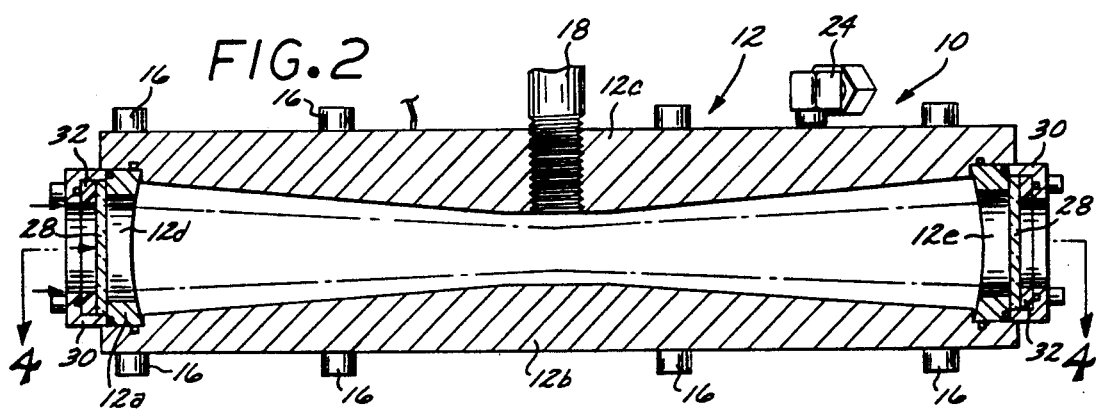

MULTIPLE-PATH GAS-ABSORPTION CELL

This is a continuation of copending application Ser. No. 07/369,460 filed on Jun. 21, 1989 now abandoned.

The present invention relates generally to spectrophotometric techniques for analyzing the content of a given gas, but more particularly to apparatus for optimizing the sensitivity of such analysis.

BACKGROUND OF THE INVENTION

Spectrophotometers have been available for a considerable number of years, and have been used to analyze the composition of various types of materials, including gases, liquids and the like. This is based on the fact that different chemical compositions absorb energy at different frequencies, so that by varying the frequency of the energy as it passes through the sample, the spectrophotometer output can identify which energy frequencies were absorbed by the sample and which were not. Thus, the chemicals present in the sample can be readily identified.

The spectrophotometer also can identify the amount of energy absorbed by the sample at each given frequency. Thus, the quantity of each chemical present in the chemical composition can be determined.

Such analysis can be performed with any one of various different ranges of energy such as infrared, ultraviolet and the like, each of which pertains to a separate range of frequencies.

Prior absorption cells for holding the sample through which the energy is passed have been capable of performing the aforedescribed analysis in conjunction with suitable spectrophotometric equipment. However, such prior cells have not been particularly sensitive in providing both quantitative and qualitative analyses. That is, prior cells have been so constructed that only a very small portion of the sample has received the energy from the spectrophotometric equipment and, as such, the sensitivity has been very minimal.

It has long been realized that to increase such sensitivity, it is desirable to pass the energy through a very large percentage of the available sample, but such prior devices have not been constructed to enable this to take place.

The present invention, on the other hand, provides a gas-absorption cell having, within the sample enclosure, a continuous reflective surface, such as a circular surface, reflecting energy back and forth, through a sample within the enclosure. By initially directing such energy flow at a predetermined angle within the enclosure, the back-and-forth reflections are caused to progress about the surface to thereby contact a substantially greater amount of the sample than could be contacted by a single pass through the sample.

OBJECTS OF THE INVENTION

In view of the foregoing, it is an object of the present invention to provide a gas-absorption cell for use with spectrophotometric equipment which enables the energy to pass through a very large percentage of the gas within the cell.

Another object of the present invention is to provide a gas-absorption cell as characterized above which is so constructed as to be small and compact while nonetheless enabling the energy to make successive passes through the gas.

Another object of the present invention is to provide a gas-absorption cell as characterized above which is so small and compact as to be easily and readily operational with existing spectrophotometric equipment without creating a bulky or large total spectrophotometric system.

Another object of the present invention is to provide a gas-absorption cell as characterized above which is formed with a generally circular interior wherein the gas sample is located, such interior being formed with one or more arcuate or circular surfaces whereby the energy can be reflected back and forth through different portions of the gas sample.

Another object of the present invention is to provide a gas-absorption cell as characterized above wherein the interior of the cell is formed with a highly polished reflective surface which is formed from a given point of curvature such that the energy reflects back and forth within the cell while successive passes are caused to progress about the interior of the cell.

A still further object of the present invention is to provide a gas-absorption cell as characterized above wherein such highly reflective surface is formed by plating silver, gold, nickel or any other appropriate material, preferably in a vapor deposition process.

Another still further object of the present invention is to provide a gas-absorption cell as characterized above wherein an optical lens is employed to direct the energy to a predetermined location on the reflective surface of the interior of the cell, whereupon the energy is reflected back and forth across the interior of the cell as such reflections successively rotate about the interior.

Another still further object of the present invention is to provide a gas-absorption cell as characterized above which can be formed as a substantially coplanar, two-dimensional device or in a spherical configuration constituting a three-dimensional device.

An even still further object of the present invention is to provide a gas-absorption cell as characterized above wherein a plurality of substantially coplanar devices can be juxtaposed and the energy, after completing its reflections in one such substantially coplanar device, is directed to other substantially coplanar devices, in succession, so that the energy is caused to pass through gas samples in each of such devices in succession.

An even still further object of the present invention is to provide a gas-absorption cell as characterized above wherein means is provided for maintaining the temperature and pressure within such cell within predetermined ranges.

An even further object of the present invention is to provide a gas-absorption cell as characterized above wherein means is provided for enabling the sample to continuously flow through the cell to enable spectrophotometric monitoring to be accomplished on a sample which is potentially constantly varying in chemical composition.

A still further object of the present invention is to provide gas-absorption cells as characterized above wherein the body or housing is formed as a sphere and wherein the spherical interior surface is highly polished and plated, and the energy is caused to traverse the interior of such cell in a three-dimensional manner such that all of the sample within the interior is ultimately exposed to the energy.

An even still further object of the present invention is to provide a gas-absorption cell as characterized above which is rugged and dependable in operation.

BRIEF DESCRIPTION OF THE DRAWINGS

The novel features which I consider characteristic of my invention are set forth with particularity in the appended claims. The invention itself, however, both as to its organization and mode of operation, together with additional objects and advantages thereof, will best be understood from the following description of specific embodiments when read in combination with the accompanying drawings, in which:

FIG. 1 is a top plan view of a gas-absorption cell according to the present invention;

FIG. 2 is a cross-sectional view taken substantially along line 2—2 of FIG. 1 of the drawings;

Like reference characters indicate corresponding parts throughout the several views of the drawings.

DESCRIPTION OF THE PREFERRED EMBODIMENT

Figure 3:
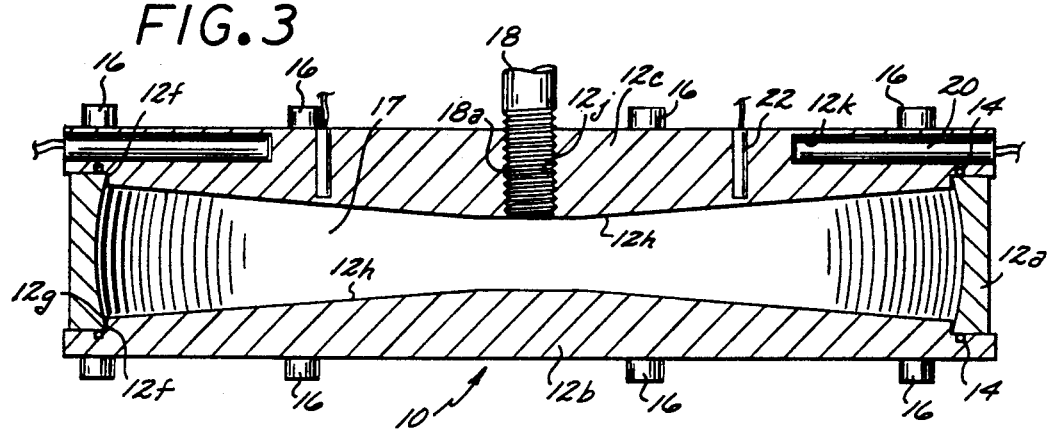
FIG. 3 is a sectional view taken substantially along line 3—3 of FIG. 1 of the drawings.

Referring to FIG. 1 of the drawings, there is shown therein a gas-absorption cell 10 according to the present invention. It comprises a housing or body 12 shown most clearly in FIGS. 2, 3 and 4 of the drawings. Such body 12 comprises an annular or circular side wall 12a, a bottom wall 12b and a top wall 12c. The side wall and top and bottom walls may be formed of any appropriate material such as aluminum or stainless steel, as will be readily apparent to those persons skilled in the art. An inlet opening 12d is formed at one given location in such side wall 12a as is an outlet opening 12e the functions of which will be hereinafter described in considerable detail.

As shown in FIGS. 2 and 3 of the drawings, the top and bottom walls 12c and 12b are formed with an annular groove 12f which individually receive an O-ring formed of appropriate material such as rubber, plastic or graphite for sealing the space between such members when they are assembled and held together by suitable fastening bolts 16. Each of the top and bottom walls is formed with an annular ledge as at 12g for locating the side wall 12a in the proper position with respect to the top and bottom walls.

For reasons which will hereinafter be explained in greater detail, the interior wall surface 12h of each of the top and bottom walls of the cell are formed at an angle such that the central portion of the circular wall is considerably thicker than the peripheral portion thereof. When the top and bottom walls are assembled to the side wall, as above noted, the slanted surfaces 12h of the top and bottom walls provide an interior cavity 17 of the cell 10 which is wider at the periphery as compared to the narrower central point thereof.

The top wall 12c is formed with a centrally located threaded opening 12j to receive and retain a pressure-sensing device 18. Such pressure-sensing device is formed with a threaded end portion 18a which sealingly fits within the opening 12j in top wall 12c.

The top wall 12c is further formed with a pair of oppositely disposed openings 12k wherein is located a pair of temperature control devices 20 which may comprise electrically energizeable heating coils for heating the top wall 12c, as will hereinafter be explained. Other openings are provided in top wall 12c for receiving temperature-sensing devices 22 which operate in conjunction with heating devices 20 to maintain the temperature of the top wall 12c within predetermined limits.

Referring most particularly to FIGS. 1 and 2 of the drawings, additional through openings are provided in the top wall 12c for threadedly receiving gas fittings 24. These are standard fittings which are available from many manufacturers and are used to bring gas samples into the absorption cell, as will hereinafter be explained in greater detail.

Positioned in each of the inlet 12d and outlet 12e is an optical lens 26 and 28, respectively. Although such lenses may be suitably positioned at the inlet and outlet of the cell 10 by use of substantially any appropriate mechanism, the form of such mechanism shown in the drawings comprises a generally cup-shaped member 30 having an annular ledge 30a and formed with a through opening 30b. A locating ring 32 is provided between the cup-shaped member 30 and the corresponding lens, there being O-rings 34 and 36 positioned in appropriate annular grooves for providing the appropriate seal around the respective lens. Suitable fastening bolts 38 are employed to fasten the lens holder to the side wall 12a so as to sealingly retain the lens over the inlet or outlet opening, as the case may be.

Figure 4:
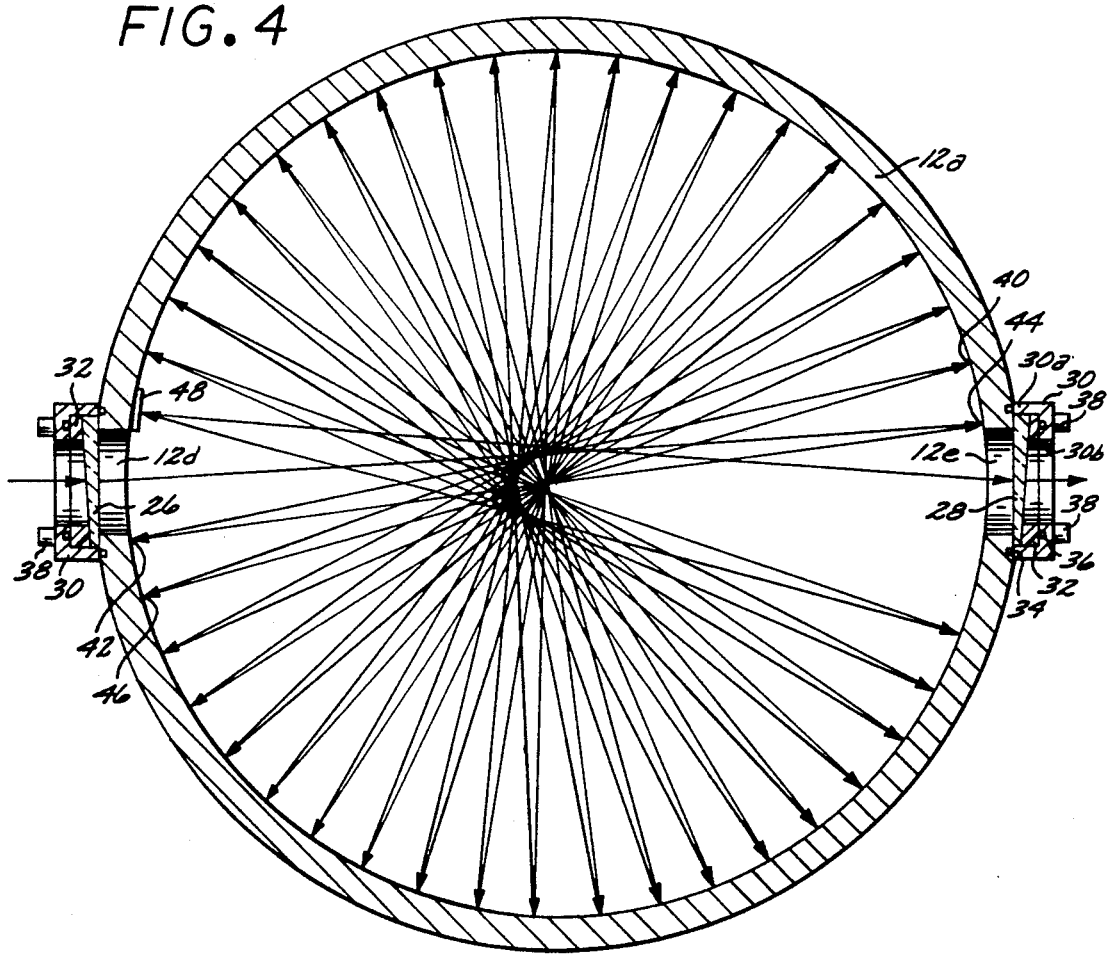
FIG. 4 is a sectional view taken substantially along line 4—4 of FIG. 2 of the drawings.

As shown in FIG. 4 of the drawings, the optical lenses 26 and 28 are tapered or wedge-shaped although being generally circular in configuration, such tapered nature being for a purpose which will be hereinafter described in greater detail.

In operation, the fittings 24 are connected to suitable conduits for delivering gaseous samples from a continually operating process (not shown) or the like. That is, it is contemplated that the instant invention has particular utility in monitoring the content of a gas which is passing through a pipe or the like, the subject apparatus being useful in providing a continuous readout of the above-mentioned spectrophotometric analyses. It is, of course, desirable to maintain the temperature and pressure within the gas cell 10 within predetermined limits corresponding to the pressure and temperature conditions of the gas prevailing in the pipe or process. Thus, as the gas is brought into the cell through one fitting 24 and its corresponding conduit, and returned to the original source of such gas through the other fitting 24 and its associated conduit, the original process or other gas source is in no way affected by the continual spectrophotometric analysis.

As the energy from the spectrophotometric equipment passes through the lens 26 and inlet opening 12d, the tapered nature of the lens directs the energy across the interior of the cell to a location such as point 40 on the interior of the side wall 12a.

The energy, as it enters the cell 10, converges toward the geometric center of the interior of the cell, and thereafter it diverges as it leaves the geometric center toward the interior wall of the side wall member 12a. For this reason, the top and bottom walls 12c and 12b are formed to provide a corresponding converging and diverging pathway, thus insuring that the energy passes through substantially all of the gas sample within the cell. Further, the tapered nature of the incoming optical lens 26 is such that the energy is directed to the opposite interior wall of the cell so as to commence the step-by-step progression of the back-and-forth reflections of such energy through the sample. That is, as the energy is reflected from the location 40 on the interior surface of side wall 12a, it is caused to reflect to the point 42 on the reflective surface, and thereafter the reflection is to point 44 and back to point 46. These back-and-forth reflections continue with the changing points of reflection causing the energy to sweep around the entire interior of the cell as it proceeds back and forth.

A reflector 48 is located at the last point of reflection for the energy to interrupt the circular progression of the reflections by directing such energy through the outlet 12e in the side wall 12a, and through the lens 28 to the spectrophotometric instrumentation for reading the energy absorption that has taken place within the cell.

As shown most particularly in FIGS. 2 and 3 of the drawings, the highly polished interior surface of the side wall 12a is curved along a vertical plane through the cell 10. Such curved nature of the reflective wall causes the reflected energy to be sent in a converging pattern toward the center of the cell where it commences to diverge as it travels toward the opposite wall section during reflection of the energy. The lenses 26 and 28 at the inlet and outlet openings 12d and 12e control the shape of such energy as it enters and leaves the cell 10.

Figure 5:
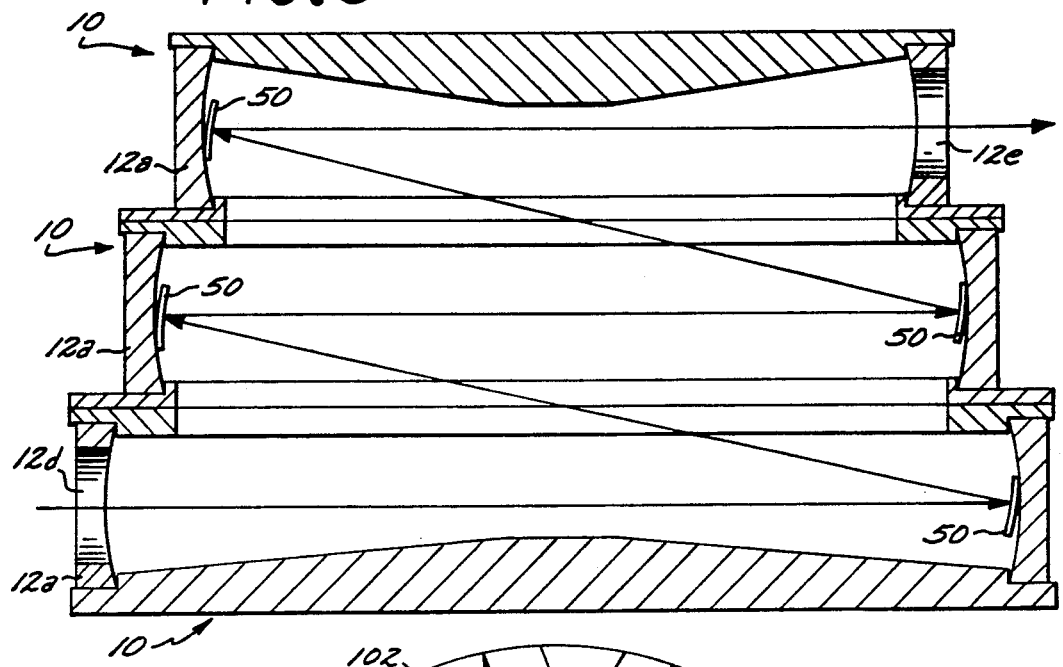
FIG. 5 is a sectional view of a gas-absorption cell comprising a plurality of substantially coplanar cells.

As shown in FIG. 5 of the drawings, two or more of such cells can be juxtaposed so as to greatly increase the amount of gas through which the energy passes before it is returned to the spectrophotometric equipment. In such event, mirrors such as shown at 50 may be employed for directing the energy from one cell to another before it is directed to an outlet opening to the energy equipment. Although the stacking arrangement shown in FIG. 5 shows cells of different diameter, it is contemplated that this is a matter of choice, and cells of like dimensions could be arranged in such superjacent position.

Figure 6:
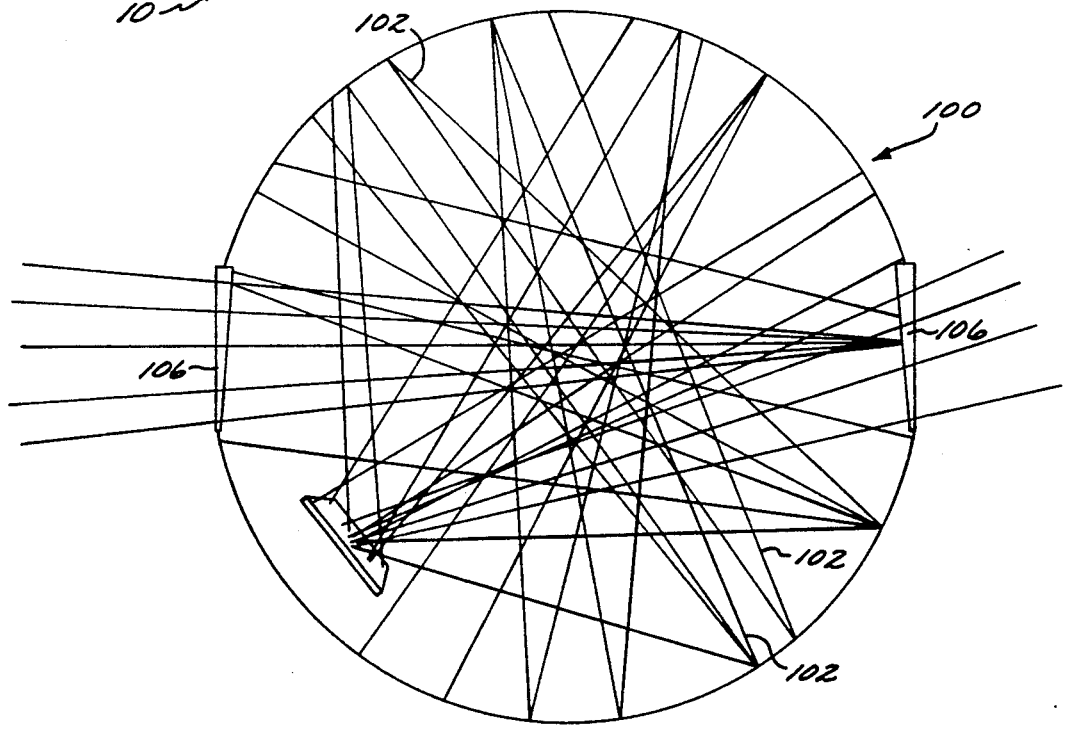
FIG. 6 is a diagrammatic showing of a generally spherical gas-absorption cell according to the present invention.

Shown in FIG. 6 is a diagram of a spherical gas-absorption cell 100 according to the present invention. Within this spherical configuration, the energy is directed along back-and-forth reflections 102 along or within a given plane and, thereafter, after completing a single revolution of reflections, is directed to another plane (not shown) as well as succeeding planes (not shown) in succession, to thereby pass through substantially all of the gas within the spherical cell 100. Such progressive steps can be accomplished with the use of mirrors, one of which is shown at 104 strategically located so as to intercept the energy at the completion of one substantially coplanar set of passes or reflections and thereby reflect such energy into a second substantially coplanar series of reflections Lenses, as shown at 106, are employed to direct the energy upon its ingress and egress to said cell 100.

Although I have shown and described certain specific embodiments of my invention, I am well aware that many modifications thereof are possible. The invention, therefore, is not to be restricted except insofar as is necessitated by the prior art and by the spirit of the appended claims.

I claim:

1. Gas-absorption apparatus for use with spectrophotometric equipment comprising, in combination, two gas-absorption cells each of which comprises a body formed with means provided an internal surface having an arcuate surface formed about a given center of curvature, each of said bodies having means for admitting gas to the interior of said body and for exhausting gases therefrom, a pair of openings in each of said cell bodies for the passage of energy into and out of the respective body, and means located in the inlet opening of one of said bodies for directing energy onto a predetermined location on the arcuate surface of the respective body whereby said energy is caused to reflect back and forth at predetermined locations on said surface so as to follow a predetermined path through the gas within the respective body and then to the outlet opening thereof, and means operatively interposed between said cells to direct the energy from the outlet opening of said one of said cells through the inlet opening of the other of said cells and onto a predetermined location non the arcuate surface of the latter cell whereby said energy is caused to travel back and forth within said other cell to the outlet thereof.

2. Gas-absorption apparatus according to claim 1 wherein the arcuate surface of each ell body is polished to reflect such energy.

3. Gas-absorption apparatus according to claim 2 wherein the arcuate surface of each cell body includes a coating of silver for reflection of said energy.

4. Gas-absorption apparatus according to claim 1 wherein the means in the inlet opening of said one of said bodies is an optical lens for directing said energy to a predetermined location on said arcuate surface of said one of said bodies.

5. Gas-absorption apparatus according to claim 1 wherein the means operatively interposed between said cells is a reflector for directing the energy to the inlet opening of said other cell body.

6. Gas-absorption apparatus according to claim 1 wherein temperature means is provided for maintaining the interior of said bodies within predetermined temperature limits.

7. Gas-absorption apparatus according to claim 6 wherein said temperature means comprises heating and cooling means and temperature sensing means associated therewith for maintaining said bodies within predetermined temperature limits.

8. Gas-absorption apparatus according to claim 1 wherein pressure means is provided for maintaining the interior of said bodies within predetermined pressure limits.

9. Gas-absorption apparatus according to claim 8 wherein said pressure means comprises pressure sensing means associated with a source of pressure for maintaining said body within predetermined pressure limits.

* * * * *